United States Patent [19]

Collins et al.

[11] 4,149,006

[45] Apr. 10, 1979

[54] PROSTAGLANDIN DERIVATIVES HAVING ALKYNYL, HYDROXY AND ARYLOXY JUNCTIONS IN THE 2β SIDE CHAIN

[75] Inventors: Paul W. Collins, Deerfield; Raphael Pappo, Skokie, both of Ill.

[73] Assignee: G. D. Searle & Co., Chicago, Ill.

[21] Appl. No.: 761,567

[22] Filed: Jan. 24, 1977

[51] Int. Cl.² .......................................... C07C 177/00
[52] U.S. Cl. ..................................... 560/53; 562/463; 562/464
[58] Field of Search ................... 560/53; 562/463, 464

[56] References Cited

FOREIGN PATENT DOCUMENTS 839533 7/1976 Belgium ..................... 260/473
7306462 11/1973 Netherlands ............... 260/473
3433474 2/1976 United Kingdom .......... 560/53

OTHER PUBLICATIONS

Derwent Abstr. 26863v/14, U.S. 3799841, 03/26/74.
Derwent Abstr. 18176y/11, BE. 846080, 03/10/77.

*Primary Examiner*—Paul J. Killos

*Attorney, Agent, or Firm*—John J. McDonnell

[57] ABSTRACT

The present invention encompasses compounds of the formula:

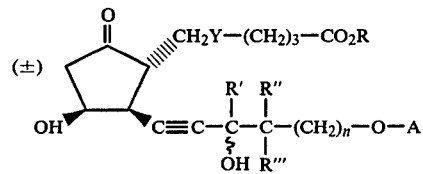

wherein n is 0 or 1; Y represents ethylene or vinylene; R represents hydrogen or lower alkyl having 1–7 carbon atoms; R', R", R''' each individually represent hydrogen or methyl; Ar represents phenyl, halosubstituted phenyl, alkyl substituted phenyl wherein the alkyl contains 1–4 carbon atoms, alkoxy substituted phenyl wherein the alkoxy contains 1–4 carbon atoms, trifluoromethylphenyl, or biphenyl; and the wavy line indicates R or S stereochemistry.

5 Claims, No Drawings

PROSTAGLANDIN DERIVATIVES HAVING ALKYNYL, HYDROXY AND ARYLOXY JUNCTIONS IN THE 2 β SIDE CHAIN

Compounds of the present invention are prepared according to the following reaction scheme.

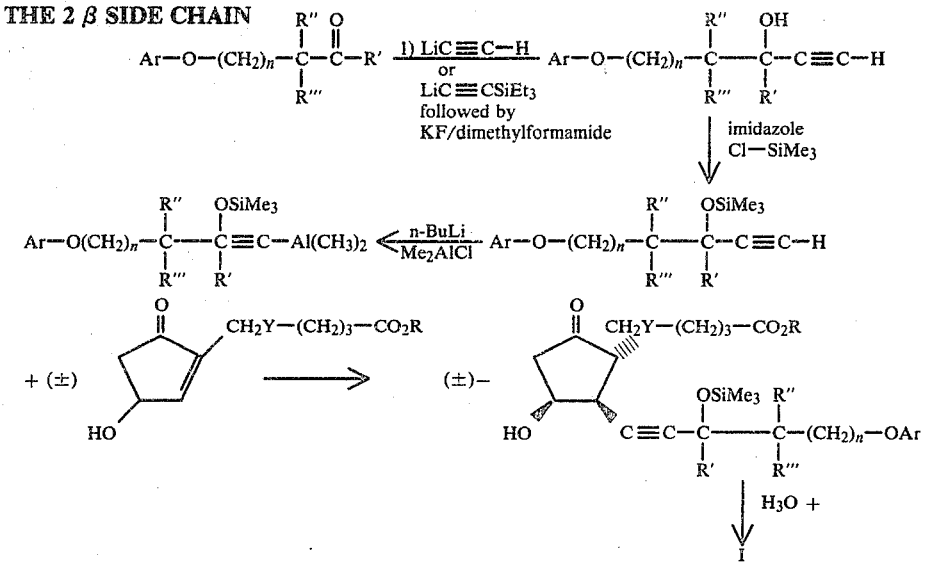

The present invention encompasses compounds of the formula:

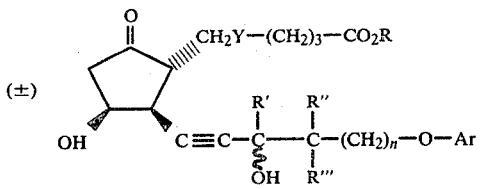

wherein n is 0 or 1; Y represents ethylene or vinylene; R represents hydrogen or lower alkyl having 1-7 carbon atoms; R', R", R''' each individually represent hydrogen or methyl; Ar represents phenyl, halosubstituted phenyl, alkyl substituted phenyl wherein the alkyl contains 1-4 carbon atoms, alkoxy substituted phenyl wherein the alkoxy contains 1-4 carbon atoms, trifluoromethylphenyl, or biphenyl; and the wavy lines indicate R or S stereochemistry.

Y may be represented by the formula —CH$_2$—CH$_2$— or —CH=CH—. Lower alkyl having 1-7 carbon atoms includes methyl, ethyl, propyl, butyl, pentyl, hexyl, and heptyl radicals and the branched chained isomers thereof.

Phenyl, chlorophenyl, fluorophenyl, bromophenyl, iodophenyl, methylphenyl, ethylphenyl, propylphenyl, isopropylphenyl, tertiarybutylphenyl, n-butylphenyl, methoxyphenyl, ethoxyphenyl, trifluoromethylphenyl are representative of Ar.

Preferred embodiments are those in which Y is —CH$_2$—CH$_2$—, R is methyl, R' is methyl, R" and R''' are hydrogen, n is zero; and Ar is as previously defined.

Also preferred are embodiments where Y is cis vinylene and other parameters are as defined in the previous paragraphs.

It should be recognized that ± designates a mixture of 3β, 2β, 1α and 3α, 2α, 1β stereochemistry on the five-membered ring and the wavy line indicates R or S configuration of the hydroxy alpha to the triple band.

Preferred embodiments are prepared as set out in Example 1.

Starting ketones are conveniently prepared by reacting acids or esters of the formula

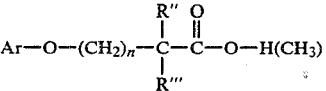

with R'Mg Br or R'Li. For example, ethyl p-chlorophenoxyisobutyrate, Merck Index, 8th edition, page 270, phenoxy propionic acid and similar compounds can be converted to the corresponding methyl ketone by methyl magnesium bromide or they can be converted to the corresponding aldehyde by the Rosenmund reaction. The acid or ethyl ester can also be reduced to the aldehyde with diisobutylaluminum hydride.

The antifertility activity of the present compounds are determined by the following test:

Sexually mature female Syrian Golden hamsters obtained from Charles River/Lakeview (9-10 weeks old) are caged with males in the late afternoon. Vaginal smears are taken daily between 8:15 and 10:00 a.m. The presence of sperm is considered positive evidence of insemination. The day of insemination is designated as day 1 of pregnancy. Pregnant females are injected daily with test compound beginning on day 1 thru day 5. Route of administration is either subcutaneous or intragastric. The test compounds and standards are administered daily on a mg/kg bodyweight basis. All animals are sacrificed with dry ice (CO$_2$) on day 7 in the morning.

The entire reproductive tract is removed and the uterus and ovaries trimmed of extraneous tissue. The total number of implantation sites is counted and recorded. By observation, day 7 size sites are designated as normal and any sites which are smaller and/or pale or resorbing are designated as abnormal.

The total number of corpora lutea are counted under a dissecting microscope and recorded. The red corpora are considered normal and the pale, pink or white regressed corpora are considered abnormal.

A single dose of compound is classified as active or inactive on the basis of the percent implantation, which is derived by dividing the total number of implantation sites by the total number of corpora lutea and multiplying by 100. 50% Or less implantation rate is considered active. 51% Or more implantation rate is considered inactive.

The $ED_{50}$ of a compound is approximated from inspection or calculated according to the method of Berkson (J. Amer. Stat. Assoc. 48 (263): 565, 1953). Estrone is employed as the standard. A relative potency can be obtained from the ratio of the $ED_{50}$ of Estrone to that of the test compound.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degrees Centigrade (° C.), and relative amounts in parts by weight, except as otherwise noted.

EXAMPLE 1

To 3.1 parts of triethylsilylacetylene in 15 parts by volume of ether at −30° C. is added 8 parts by volume of 2.5 molar n-butyl lithium. The reaction mixture is allowed to come to room temperature and 3 parts of phenoxyacetone in 5 parts by volume of ether is added. The reaction mixture is stirred at room temperature for one hour and then poured into ether and dilute (1 N) hydrochloric acid solution. The ether layer is washed with water and dried over anhydrous sodium sulfate. The solvents are removed at reduced pressure and the residual oil is dissolved in 15 parts by volume of dimethylformamide containing about 5 parts of powdered potassium fluoride. The reaction mixture is stirred at 70°–80° C. for about 1 hour. The reaction mixture is worked up by diluting with ether and washing several times with water. The ether layer is dried over anhydrous sodium sulfate and stripped of solvent under reduced pressure. The residual oil is isolated by low pressure liquid chromatography on silica gel using 30% ethyl acetate/hexane as eluent to provide 3-hydroxy-3-methyl-4-phenoxy-1-butyne.

The hydroxyl group of this alkyne is protected by dissolving 2 parts of the butyne in 5 parts by volume of dimethylformamide and successively treating the reaction mixture with 2 parts of imidazole and 1.2 parts of trimethylsilylchloride. The reaction mixture is stirred at room temperature for 1 hour and poured into ether/water. The ethereal layer is washed with water and dried over anhydrous sodium sulfate. Isolation by low pressure liquid chromatography on silica gel provides 3-methyl-3-trimethylsilyloxy-4-phenoxy-1-butyne.

To 2.65 parts of this protected alkyne in 10 parts by volume of ethyl ether at −40° is added 4.6 parts by volume of 2.17 molar butyl lithium. The reaction mixture is allowed to warm to room temperature and is stirred at room temperature for 30 minutes. The reaction mixture is recooled to −40° C. and then treated with 6.16 parts of a 15% solution of dimethylaluminum chloride in heptane and the resulting reaction mixture is allowed to warm to room temperature. 1.5 Parts of methyl 7-(3-hydroxy-5-oxocyclopent-1-yl)heptanoate in 5 parts by volume of ethyl ether is added. The reaction mixture is stirred at room temperature for 1–2 hours and poured into ether/dilute hydrochloric acid. The ethereal layer is washed with water and dried over anhydrous sodium sulfate. The ether is removed and the residual oil is chromatographed on silica gel to provide methyl 7-[3β-hydroxy-2β-(3RS-trimethylsilyloxy-3-methyl-4-phenoxy-1-butyn-1-yl)-5-oxocyclopent-1α-yl]heptanoate which is eluted with 30% ethyl acetate/hexane.

0.8 Part of this product is stirred overnight in 10 parts by volume of a 3:1:1 mixture of acetic acid/water/tetrahydrofuran to hydrolyze the trimethylsilyl group. The reaction mixture is poured into ether/water and the ethereal layer is washed with water several times and dried over anhydrous sodium sulfate. Low pressure liquid chromatography using 100% ethyl acetate as the eluent provides racemic methyl 7-[3β-hydroxy-2β-(3RS-hydroxy-3-methyl-4-phenoxy-1-butyn-1-yl)-5-oxocyclopent-1α-yl]heptanoate having the following structural formula:

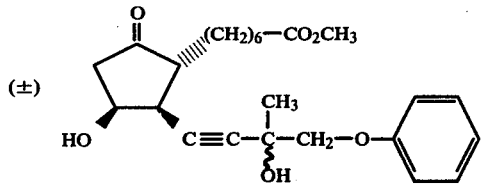

Replacing phenoxyacetone in Example 1 with an equivalent quantity of p-methylphenoxyacetone provides racemic methyl 7-[3β-hydroxy-2β-(3RS-hydroxy-3-methyl-4-p-methylphenoxy-1-butyn-1-yl)-5-oxocyclopent-1α-yl]heptanoate.

Replacing phenoxyacetone in Example 1 with an equivalent quantity of p-fluorophenoxyacetone provides racemic methyl 7-[3β-hydroxy-2β-(3RS-hydroxy-3-methyl-4-p-fluorophenoxy-1-butyn-1-yl)-5-oxocyclopent-1α-yl]heptanoate.

Replacing phenoxyacetone in Example 1 with an equivalent quantity of p-ethylphenoxyacetone provides racemic methyl 7-[3β-hydroxy-2β-(3RS-hydroxy-3-methyl-4-p-ethylphenoxy-1-butyn-1-yl)-5-oxocyclopent-1α-yl]heptanoate.

Replacing phenoxyacetone in Example 1 with an equivalent quantity of p-phenylphenoxyacetone provides racemic methyl 7-[3β-hydroxy-2β-(3RS-hydroxy-3-methyl-4-phenylphenoxy-1-butyn-1-yl)-5-oxocyclopent-1α-yl]heptanoate.

Replacing phenoxyacetone in Example 1 with an equivalent quantity of p-trifluoromethylphenoxyacetone provides racemic methyl 7-[3β-hydroxy-2β-(3RS-hydroxy-3-methyl-4-p-trifluoromethylphenoxy-1-butyn-1-yl)-5-oxocyclopent-1α-yl]heptanoate.

Replacing phenoxyacetone in Example 1 with an equivalent quantity of p-chlorophenoxyacetone provides racemic methyl 7-[3β-hydroxy-2β-(3RS-hydroxy-3-methyl-4-p-chlorophenoxy-1-butyn-1-yl)-5-oxocyclopent-1α-yl]heptanoate.

Replacing phenoxyacetone in Example 1 with an equivalent quantity of p-methoxyphenoxyacetone provides racemic methyl 7-[3β-hydroxy-2β-(3RS-hydroxy-3-methyl-4-p-methoxyphenoxy-1-butyn-1-yl)-5-oxocyclopent-1α-yl]heptanoate.

EXAMPLE 2

Following the procedure of Example 1, replacing phenoxyacetone with α,α-dimethylphenoxyacetaldehyde and using 7-(3(RS)-hydroxy-5-oxocyclopent-1-en- 1-yl)hept-5-cisenoate provides racemic methyl 7-[3β-hydroxy-2β-(3RS-hydroxy-4,4-dimethyl-4-phenoxy-1-butyn-1-yl)-5-oxocyclopent-1α-yl]hept-5-cis-enoate having the following structural formula:

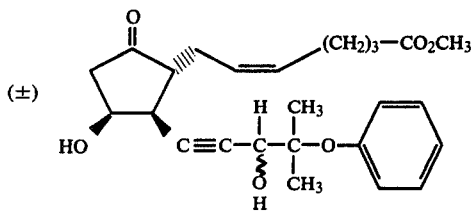

EXAMPLE 3

Following the procedure set out in Example 1 using equivalent quantities of 7-(3-hydroxy-5-oxocyclopent-1-yl)heptanoic acid provides racemic 7-[3β-hydroxy-2β-(3RS-hydroxy-3-methyl-4-phenoxy-1-butyn-1-yl)-5-oxocyclopent-1α-yl]heptanoic acid having the following structural formula:

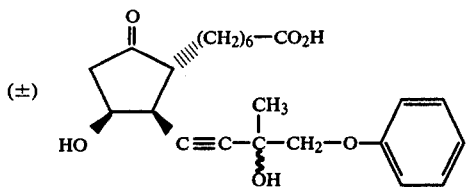

What is claimed is:

1. A compound of the formula

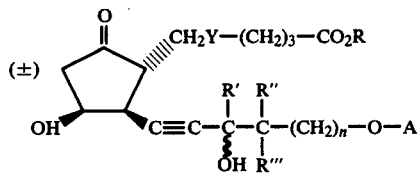

wherein n is 0 or 1, Y represents ethylene or vinylene; R represents hydrogen or lower alkyl having 1-7 carbon atoms; R', R", R''' each independently represent hydrogen or methyl; Ar represents phenyl, halosubstituted phenyl, alkyl substituted phenyl wherein the alkyl contains 1-4 carbon atoms, alkoxy substituted phenyl wherein the alkoxy contains 1-4 carbon atoms, trifluoromethylphenyl or biphenyl.

2. A compound according to claim 1 having the formula:

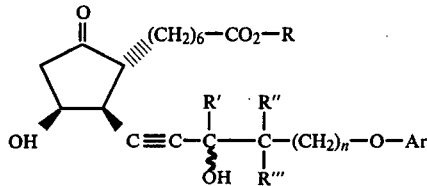

wherein n is 0 or 1; R represents hydrogen or lower alkyl having 1-7 carbon atoms; R, R", and R''' each individually represent hydrogen or methyl; Ar represents phenyl, halosubstituted phenyl, alkyl substituted phenyl wherein the alkyl contains 1-4 carbon atoms, alkoxy substituted phenyl wherein the alkoxy contains 1-4 carbon atoms, trifluoromethylphenyl or biphenyl.

3. A compound according to claim 1 having the formula:

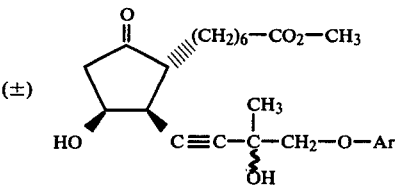

wherein Ar represents phenyl, halosubstituted phenyl, alkylsubstituted phenyl wherein the alkyl contains 1-4 carbon atoms, alkoxy substituted phenyl wherein the alkoxy contains 1-4 carbon atoms, trifluoromethylphenyl or biphenyl.

4. A compound according to claim 1 which is racemic methyl 7-[3β-hydroxy-2β-(3RS-hydroxy-3-methyl-4-phenoxy-1-butyn-1-yl)-5-oxocyclopent-1α-yl]heptanoate.

5. A compound according to claim 1 which is racemic methyl 7-[3β-hydroxy-2β-(3RS-hydroxy-3-methyl-4-p-fluorophenoxy-1-butyn-1-yl)-5-oxocyclopent-1α-yl]heptanoate.

* * * * *